(12) United States Patent
Machinaga et al.

(10) Patent No.: US 9,120,835 B2
(45) Date of Patent: Sep. 1, 2015

(54) PHOSPHORIC ACID ESTER DERIVATIVES

(75) Inventors: Nobuo Machinaga, Tokyo (JP); Jun Chiba, Tokyo (JP); Ryuji Hashimoto, Tokyo (JP); Mamoru Otoyo, Tokyo (JP); Ryotaku Inoue, Tokyo (JP)

(73) Assignee: Daiichi Sankyo Company Limited, Tokyo (JP)

( * ) Notice: Subject to any disclaimer, the term of this patent is extended or adjusted under 35 U.S.C. 154(b) by 60 days.

(21) Appl. No.: 14/129,596

(22) PCT Filed: Jun. 27, 2012

(86) PCT No.: PCT/JP2012/066357
§ 371 (c)(1),
(2), (4) Date: Dec. 27, 2013

(87) PCT Pub. No.: WO2013/002248
PCT Pub. Date: Jan. 3, 2013

(65) Prior Publication Data
US 2014/0135292 A1 May 15, 2014

(30) Foreign Application Priority Data
Jun. 28, 2011 (JP) ................. 2011-142617

(51) Int. Cl.
*C07F 9/6506* (2006.01)
*C07F 9/6558* (2006.01)
*C07F 7/18* (2006.01)
*C07F 9/572* (2006.01)

(52) U.S. Cl.
CPC ........... *C07F 9/65062* (2013.01); *C07F 7/1844* (2013.01); *C07F 7/1856* (2013.01); *C07F 9/572* (2012.01); *C07F 9/65065* (2013.01); *C07F 9/65583* (2013.01)

(58) Field of Classification Search
CPC ................ C07F 9/65062; C07F 9/95583
See application file for complete search history.

(56) References Cited

U.S. PATENT DOCUMENTS

| 7,649,098 | B2 | 1/2010 | Augeri et al. |
| 8,404,732 | B2 | 3/2013 | Augeri et al. |
| 8,653,126 | B2 | 2/2014 | Machinaga et al. |
| 2002/0042091 | A1 | 4/2002 | Normant et al. |
| 2009/0298901 | A1 | 12/2009 | Wu et al. |
| 2009/0318516 | A1 | 12/2009 | Burgoon et al. |
| 2012/0316170 | A1 | 12/2012 | Machinaga et al. |
| 2013/0102008 | A1 | 4/2013 | Otoyo et al. |

FOREIGN PATENT DOCUMENTS

| JP | 2001-518303 A | 10/2001 |
| JP | 2004-509638 A | 4/2004 |
| JP | 2005-531285 A | 10/2005 |
| JP | 2008-530135 A | 8/2008 |
| JP | 2009-527564 A | 7/2009 |
| WO | WO 84/03441 A1 | 9/1984 |
| WO | WO 97/46543 A1 | 12/1997 |
| WO | WO 99/16888 A2 | 4/1999 |
| WO | WO 02/27318 A1 | 4/2002 |
| WO | WO 03/062390 A2 | 7/2003 |
| WO | WO 2006/088944 A1 | 8/2006 |
| WO | WO 2007/100617 A2 | 9/2007 |
| WO | WO 2008/109314 A1 | 9/2008 |
| WO | WO 2008/128045 A1 | 10/2008 |
| WO | WO 2011/102404 A1 | 8/2011 |

OTHER PUBLICATIONS

Bushey et al. "Intramolecular Nitrogen-Phosphorus Interactions of Phosphate Esters" Journal of Organic Chemistry, 1985, vol. 50, pp. 2091-2095.*
Bagdanoff et al., "Inhibition of Sphingosine-1-Phosphate Lyase for the Treatment of Autoimmune Disorders," *J. Med. Chem.*, 52:3941-3953 (2009).
Bagdanoff et al., Inhibition of Sphingosine 1-Phosphate Lyase for the Treatment of Rheumatoid Arthritis: Discovery of (E)-1-(4-((1R,2S,3R)-1,2,3,4-Tetrahydroxybutyl)-1H-imidazol-2-yl)ethanone Oxime (LX2931) and (1R,2S,3R)-1-(2-(Isoxazol-3-yl)-1H-imidazol-4-yl)butane-1,2,3,4-tetraol (LX2932), *J. Med. Chem.*, 53:8650-8662 (2010).
Bandhuvula et al., "A rapid fluorescence assay for sphingosine-1-phosphate lyase enzyme activity," *Journal of Lipid Research*, 48:2769-2778 (2007).
Bandhuvula et al., "Sphingosine 1-phosphate lyase enzyme assay using a BODIPY-labeled substrate," *Biochemical and Biophysical Research Communications*, 380:366-370 (2009).
Bedia et al., "Synthesis of a Fluorogenic Analogue of Sphingosine-1-Phosphate and Its Use to Determine Sphingosine-1-Phosphate Lyase Activity," *Chembiochem*, 10:820-822 (2009).
Edsall et al., "Enzymatic Measurement of Sphingosine 1-Phosphate," *Analytical Biochemistry*, 272:80-86 (1999).
Gilenya® Product Data Sheet, Novartis Pharmaceuticals Corp., East Hanover, New Jersey, USA, 2012, 17 pages.
Kim et al., "Elevation of Sphingoid Base 1-Phosphate as a Potential Contributor to Hepatotoxicity in Fumonisin $B_1$-Exposed Mice," *Arch. Pharm. Res.*, 30(8):962-969 (2007).
Kumar et al., "Lyase to live by: Sphingosine phosphate lyase as a therapeutic target," *Expert Opin. Ther. Targets*, 13(8):1013-1025 (2009).
Le Stunff et al., "Role of Sphingosine-1-phosphate Phosphatase 1 in Epidermal Growth Factor-induced Chemotaxis," *The Journal of Biological Chemistry*, 279(33):34290-34297 (2004).

(Continued)

*Primary Examiner* — Joseph Kosack
(74) *Attorney, Agent, or Firm* — Dorsey and Whitney LLP

(57) ABSTRACT

To provide a novel compound that has S1P lyase inhibitory ability and induces a reduction in the number of lymphocytes, or a pharmaceutically acceptable salt thereof, and a pharmaceutical composition containing the compound or pharmaceutically acceptable salt thereof as an active ingredient. A compound represented by the general formula (I):

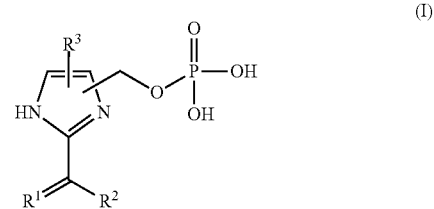

or a pharmaceutically acceptable salt thereof.

16 Claims, No Drawings

(56) References Cited

OTHER PUBLICATIONS

Lee et al., "A novel method to quantify sphingosine 1-phosphate by immobilized metal affinity chromatography (IMAC)," *Prostaglandins & other Lipid Mediators*, 84:154-162 (2007).

Mandala et al., "Alteration of Lymphocyte Trafficking by Sphingosine-1-Phosphate Receptor Agonists," *Science*, 296:346-349 (2002).

Murata et al., "Quantitative Measurement of Sphingosine 1-Phosphate by Radioreceptor-Binding Assay," *Analytical Biochemistry*, 282:115-120 (2000).

Reiss et al., "Sphingosine-phosphate Lyase Enhances Stress-induced Ceramide Generation and Apoptosis," *The Journal of Biological Chemistry*, 279(2):1281-1290 (2004).

Schwab et al., "Lymphocyte Sequestration Through S1P Lyase Inhibition and Disruption of S1P Gradients," *Science*, 309:1735-1739 (2005).

Serra et al., "Sphingosine 1-phosphate lyase, a key regulator of sphingosine 1-phosphate signaling and function," *Advances in Enzyme Regulation*, 50:349-362 (2010).

Vogel et al., "Incomplete Inhibition of Sphingosine 1-Phosphate Lyase Modulates Immune System Function yet Prevents Early Lethality and Non-Lymphoid Lesions," *PLoS One*, vol. 4, Issue 1, e4112, 15 pages (2009).

Yatomi et al., "Quantitative Measurement of Sphingosine 1-Phosphate in Biological Samples by Acylation with Radioactive Acetic Anhydride," Analytical Biochemistry, 230:315-320 (1995).

Yu et al., "Pharmacokinetic/pharmacodynamic modelling of 2-acetyl-4(5)-tetrahydroxybutyl imidazole-induced peripheral lymphocyte sequestration through increasing lymphoid sphingosine 1-phosphate," *Xenobiotica*, 40(5):350-356 (2010).

English translation of International Search Report issued on Mar. 29, 2011, in PCT Application No. PCT/JP2011/053336, 3 pages.

English translation of International Search Report issued on Sep. 13, 2011, in PCT Application No. PCT/JP2011/064535, 2 pages.

English translation of International Search Report issued on Sep. 4, 2012, in PCT Application No. PCT/JP2012/066357, 4 pages.

Non-Final Office Action mailed May 17, 2013, U.S. Appl. No. 13/579,791, 18 pages.

Response to Non-Final Office Action filed Sep. 3, 2013, U.S. Appl. No. 13/579,791, 12 pages.

Notice of Allowance mailed Oct. 11, 2013, U.S. Appl. No. 13/579,791, 11 pages.

Restriction Requirement mailed Dec. 6, 2013, U.S. Appl. No. 13/805,787, 6 pages.

Response to Restriction Requirement filed Dec. 26, 2013, U.S. Appl. No. 13/805,787, 6 pages.

Bushey et al., "Intramolecular Nitrogen-Phosphorus Interactions of Phosphate Esters," *J. Org. Chem.*, (1985), 50:2091-2095.

Ohtoyo et al., "Sphingosine 1-phosphate lyase inhibition by 2-acetyl-4-(tetrahydroxybutyl)imidazole (THI) under conditions of vitamin B6 deficiency," *Mol. Cell Biochem.*, Nov. 9, 2014, 9 pages.

Supplementary European Search Report issued on Feb. 3, 2015, in European Patent Application No. 12 80 4846, 7 pages.

Office Action issued on Jan. 12, 2015, in U.S. Appl. No. 13/805,787, 10 pages.

Desai et al., "Fumonisins and fumonisin analogs as inhibitors of ceramide synthase and inducers of apoptosis," *Biochimica et Biophysica Acta*, (2002), 1585:188-192.

Melendez, "Sphingosine kinase signalling in immune cells: Potential as novel therapeutic targets," *Biochimica et Biophysica Acta*, (2008), 1784:66-75.

Van Veldhoven et al., "Sphinganine 1-phosphate metabolism in cultured skin fibroblasts: evidence for the existence of a sphingosine phosphatase," *Biochem. J.*, (1994), 299:597-601.

Non-Final Office Action issued Jun. 20, 2014, U.S. Appl. No. 13/805,787, 15 pages.

\* cited by examiner

PHOSPHORIC ACID ESTER DERIVATIVES

This application is a national stage application under 35 U.S.C. §371 of International Application No. PCT/JP2012/066357, filed Jun. 27, 2012, entitled "Phosphoric Acid Ester Derivative," which claims priority to Japanese Patent Application No. 2011-142617, filed Jun. 28, 2011, the contents of all of which are hereby incorporated in their entirety by reference.

TECHNICAL FIELD

The present invention relates to a novel phosphoric acid ester derivative having sphingosine-1-phosphate (hereinafter sometimes referred to as S1P) lyase inhibitory activity and having an effect of reducing the number of lymphocytes, or a pharmaceutically acceptable salt thereof, and to a pharmaceutical composition containing the derivative or salt as an active ingredient.

BACKGROUND ART

As immunosuppressive agents, for example, cyclosporin, tacrolimus and the like that suppress the production of cytokines such as IL-2 are currently utilized. Furthermore, in recent years, compounds that suppress the activity of the immune system by inducing a decrease in the number of lymphocytes in the blood have been studied. For example, fingolimod does not show an action to suppress the production of cytokines in vitro, but is phosphorylated in the biological body and then acts as an S1P receptor agonist to thereby induce a decrease in the number of lymphocytes in the blood. By this way, the activity of the immune system is suppressed (for example, see Non-Patent Literature 1).

As a compound that induces a reduction in the number of lymphocytes in the blood by a mechanism other than that of S1P receptor agonists, 2-acetyl-4-tetrahydroxybutylimidazole (THI) is known (for example, see Patent Literature 1). THI induces a reduction in the number of lymphocytes in the blood by inhibiting S1P lyase (for example, see Non-Patent Literature 2, Non-Patent Literature 3 and the like).

As such S1P lyase inhibitors, besides THI, imidazole derivatives having a polyol as a substituent (for example, see Patent Literature 2, Patent Literature 3, Non-Patent Literature 4, Non-Patent Literature 5 and the like), imidazole derivatives to which a hetero ring is directly bound (for example, see Patent Literature 4, Patent Literature 5, Non-Patent Literature 4, Non-Patent Literature 5 and the like), and the like are known. Furthermore, as compounds that induce a reduction in the number of lymphocytes, thiazole derivatives having a polyol as a substituent (for example, see Patent Literature 6) and the like are known.

CITATION LIST

Patent Literature

Patent Literature 1: WO 84/03441
Patent Literature 2: WO 2007/100617
Patent Literature 3: WO 2008/128045
Patent Literature 4: WO 2008/109314
Patent Literature 5: US2009/0318516
Patent Literature 6: WO 97/46543
Patent Literature 7: WO 2011/102404

Non-Patent Literature

Non-Patent Literature 1: Science, 296, 346-349 (2002)
Non-Patent Literature 2: Science, 309, 1735-1739 (2005)
Non-Patent Literature 3: Xenobiotica, 2010; 40 (5): 350-356
Non-Patent Literature 4: J. Med. Chem. 2009, 52, 3941-3953
Non-Patent Literature 5: J. Med. Chem. 2010, 53, 8650-8662

SUMMARY OF INVENTION

Technical Problem

However, none of the above-mentioned Patent Literatures 1 to 7 and Non-Patent Literatures 1 to 5 specifically describes the compound of the present invention.

Therefore, the present invention aims at providing a novel compound that has S1P lyase inhibitory ability and induces a reduction in the number of lymphocytes, or a pharmaceutically acceptable salt thereof, and providing a pharmaceutical composition containing these as an active ingredient.

Solution to Problem

The present invention provides
(1) a compound represented by the general formula (I):

[Chemical Formula 1]

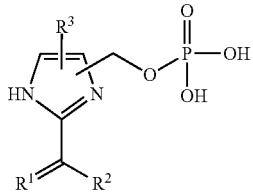

(I)

wherein
$R^1$ is an oxygen atom or N—OH,
$R^2$ is a methyl group, or
$R^1$ and $R^2$ together with the carbon atom to which they are bonded form

[Chemical Formula 2]

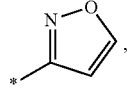

, and
$R^3$ is a hydrogen atom or a methyl group,
or an isotope thereof, or a pharmaceutically acceptable salt thereof;
(2) a compound selected from the group consisting of:
phosphoric acid mono-(2-acetyl-1H-imidazol-4-ylmethyl) ester,
phosphoric acid mono-(2-acetyl-3H-imidazol-4-ylmethyl) ester,
phosphoric acid mono-(2-acetyl-5-methyl-1H-imidazol-4-ylmethyl) ester,
phosphoric acid mono-(2-acetyl-5-methyl-3H-imidazol-4-ylmethyl) ester,
phosphoric acid mono-(2-{1-[(Z)-hydroxyimino]-ethyl}-1H-imidazol-4-ylmethyl) ester,
phosphoric acid mono-(2-{1-[(Z)-hydroxyimino]-ethyl}-3H-imidazol-4-ylmethyl) ester,
phosphoric acid mono-(2-{1-[(E)-hydroxyimino]-ethyl}-1H-imidazol-4-ylmethyl) ester, phosphoric acid mono-(2-{1-[(E)-hydroxyimino]-ethyl}-3H-imidazol-4-ylmethyl) ester, phosphoric acid mono-(2-isoxazol-3-yl-1H-imidazol-4-ylmethyl) ester and phosphoric acid mono-(2-isoxazol-3-yl-3H-imidazol-4-ylmethyl) ester, or an isotope thereof, or a pharmaceutically acceptable salt thereof;

(3) a pharmaceutical composition containing the compound or isotope thereof, or pharmaceutically acceptable salt thereof according to the above-mentioned (1) or (2) as an active ingredient;

(4) the pharmaceutical composition according to the above-mentioned (3), for use in preventing or treating an inflammatory bowel disease, an acute pulmonary disorder, an ischemia-reperfusion disorder, an autoimmune disease, multiple sclerosis or an allergic disease, or for suppressing implant rejection response;

(5) the pharmaceutical composition according to the above-mentioned (4), wherein the inflammatory bowel disease is ulcerative colitis or Crohn's disease;

(6) the pharmaceutical composition according to the above-mentioned (4), wherein the autoimmune disease is rheumatoid arthritis, systemic lupus erythematosus, psoriasis, antiphospholipidantibodysyndrome, polymyositis, dermatomyositis, systemic sclerema, Sjogren's syndrome, polyarteritis nodosa, microscopic polyarteritis, allergic granulomatous angiitis, Wegener's granulomatosis or mixed connective tissue disease;

(7) the pharmaceutical composition according to the above-mentioned (4), wherein the allergic disease is atopic dermatitis, allergic rhinitis, pollinosis, allergic conjunctivitis, allergic gastroenteritis, bronchial asthma, infantile asthma, food allergy, drug allergy or urticaria;

(8) use of the compound or isotope thereof, or pharmaceutically acceptable salt thereof according to the above-mentioned (1) or (2) for producing a pharmaceutical composition for preventing or treating an inflammatory bowel disease, an acute pulmonary disorder, an ischemia-reperfusion disorder, an autoimmune disease, multiple sclerosis or an allergic disease, or for suppressing implant rejection response;

(9) a method for preventing or treating an inflammatory bowel disease, an acute pulmonary disorder, an ischemia-reperfusion disorder, an autoimmune disease, multiple sclerosis or an allergic disease, or for suppressing implant rejection response, including administering a therapeutically effective amount of the compound or isotope thereof, or pharmaceutically acceptable salt thereof according to the above-mentioned (1) or (2) to a mammal; and

(10) the method according to the above-mentioned (9), wherein the mammal is a human.

Advantageous Effects of Invention

The compound or pharmaceutically acceptable salt thereof of the present invention has excellent S1P lyase inhibitory ability and exerts an effect of reducing the number of lymphocytes in the blood in vivo. Furthermore, the pharmaceutical composition of the present invention exerts an effect that the composition can treat or prevent inflammatory bowel diseases, acute pulmonary disorders, ischemia-reperfusion disorders, autoimmune diseases, multiple sclerosis, allergic diseases and the like and can suppress implant rejection response in mammals, specifically humans.

DESCRIPTION OF EMBODIMENTS

In the present specification, "pharmaceutically acceptable salt" refers to a salt that is formed by reacting the compound of the present invention with an acid or a base.

Examples of the salt may include hydrohalide acid salts such as hydrofluoric acid salts, hydrochloric acid salts, hydrobromic acid salts and hydroiodic acid salts; inorganic acid salts such as hydrochloric acid salts, nitric acid salts, perchloric acid salts, sulfuric acid salts and phosphoric acid salts; lower alkanesulfonic acid salts such as methanesulfonic acid salts, trifluoromethanesulfonic acid salts and ethanesulfonic acid salts; arylsulfonic acid salts such as benzenesulfonic acid salts and p-toluenesulfonic acid salts; organic acid salts such as acetic acid salts, malic acid salts, fumaric acid salts, succinic acid salts, citric acid salts, ascorbic acid salts, tartaric acid salts, oxalic acid salts and maleic acid salts; alkali metal salts such as sodium salts, potassium salts and lithium salts; alkaline earth metal salts such as calcium salts and magnesium salts; metal salts such as aluminum salts and iron salts; inorganic salts such as ammonium salts; amine salts such as organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; and amino acid salts such as glycine salts, lysine salts, arginine salts, ornithine salts, glutamic acid salts and aspartic acid salts.

In some cases, the compound of the present invention becomes a hydrate by, for example, absorbing moisture to contain adsorbed water attached thereto by being left in the air, and such hydrates are also encompassed by the salt of the present invention.

In the case where tautomers of the imidazole ring are present, the compound of the present invention encompasses all of the respective tautomers and mixtures thereof at any ratio.

Furthermore, the present invention may encompass compounds in which one or more atom(s) constituting the compound of the present invention is/are substituted with isotope(s) of the atom(s). There are two kinds of isotopes: radioactive isotopes and stable isotopes, and examples of the isotopes may include hydrogen isotopes ($^2$H and $^3$H), carbon isotopes ($^{11}$C, $^{13}$C and $^{14}$C), nitrogen isotopes ($^{13}$N and $^{15}$N), oxygen isotopes ($^{15}$O, $^{17}$ and $^{18}$O), and fluorine isotopes ($^{18}$F). A composition containing a compound labeled with isotope(s) is useful as, for example, a therapeutic agent, a prophylactic agent, a research reagent, an assay reagent, a diagnostic agent, an in-vivo image diagnostic agent or the like. Compounds labeled with isotope(s) are also encompassed in the compound of the present invention, and all mixtures of compounds labeled with isotope(s) at any ratio are also encompassed in the compound of the present invention. Furthermore, the compound labeled with isotope(s) of the present invention can be produced by methods known in the art, for example, by using a raw material labeled with isotope(s) instead of the raw material in the production methods of the present invention mentioned below.

The compound of the present invention can easily be prepared from, for example, known compounds according to the Reference Examples, Examples and Preparation Examples mentioned below.

The compound or pharmaceutically acceptable salt thereof of the present invention obtained by the above-mentioned methods has excellent S1P lyase inhibitory ability and reduces the number of lymphocytes, and thus can suppress the activity of the immune system. Therefore, the compound or the pharmaceutically acceptable salt thereof of the present invention can be used as an active ingredient for a pharmaceutical composition for preventing or treating inflammatory bowel diseases (IBDs) (for example, ulcerative colitis, Crohn's disease and the like), acute pulmonary disorders, ischemia-reperfusion disorders (for example, heart, brain, liver, kidneys, lungs and the like), autoimmune diseases (for example, rheumatoid arthritis, systemic lupus erythematosus, psoriasis, antiphospholipid antibody syndrome, polymyositis, dermatomyositis, systemic sclerema, Sjogren's syndrome, polyarteritis nodosa, microscopic polyarteritis, allergic granulomatous angiitis, Wegener's granulomatosis, mixed connective tissue disease and the like), multiple sclerosis (MS), allergic diseases (for example, atopic dermatitis, allergic rhinitis (including pollinosis), allergic conjunctivitis, allergic gastroenteritis, bronchial asthma, infantile asthma, food allergy, drug allergy, urticaria and the like) and the like or for suppressing implant rejection responses.

In the case where the pharmaceutical composition containing the compound of the present invention or pharmaceutically acceptable salt thereof as an active ingredient is administered to a mammal (for example, a human, a horse, a cattle, a swine or the like, preferably a human), the composition may be administered systemically or topically, and orally or parenterally.

The pharmaceutical composition of the present invention can be prepared by selecting a suitable form depending on the administration method according to various conventionally-used processes for the preparation of formulations.

Examples of forms of oral pharmaceutical composition may include a tablet agent, a pill agent, a powder agent, a granular agent, a capsule agent, an aqueous agent, a suspension agent, an emulsion agent, a syrup agent, and an elixir agent. The preparation of pharmaceutical compositions having such forms may be prepared according to conventional methods by suitably selecting an excipient, a binder agent, a disintegrant, a lubricant, a swelling agent, a swelling aid, a coating agent, a plasticizer, a stabilizer, an antiseptic agent, an antioxidant, a colorant, a dissolution aid, a suspending agent, an emulsifier, a sweetener, a preservative, a buffer agent, a diluting agent, a wetting and the like, which are generally used as additives, as necessary.

Examples of forms of parenteral pharmaceutical composition may include an injection agent, an ointment agent, a gel agent, a cream agent, a wet dressing agent, a patch, an aerosolized agent, an inhalation agent, a spray agent, an ophthalmic preparation, a nasal preparation, a suppository, and an inhalation agent. Pharmaceutical compositions having such forms can be prepared according to conventional methods by suitably selecting a stabilizer, an antiseptic agent, a dissolution aid, a moisture agent, a preservative, an antioxidant, a flavoring agent, a gelation agent, a neutralizing agent, a dissolution aid, a buffer agent, an isotonic agent, a surfactant, a colorant, a buffering agent, a thickening agent, a wetting agent, a filler, an absorption promoter, a suspending agent, a binder and the like, which are generally used as additives, as necessary.

The dose of the compound of the present invention or pharmaceutically acceptable salt thereof differs depending on symptoms, age, body weight and the like; in the case of oral administration, the dose is 1 to 3,000 mg, preferably 1 to 1,000 mg in terms of the amount of the compound per one time per one adult human, once to several times a day; in the case of parenteral administration, the dose is 0.01 to 1,500 mg, preferably 0.1 to 500 mg in terms of the amount of the compound per one time per one adult human, once to several times a day.

Hereinafter the present invention will further be explained in more detail with reference to the Reference Examples, Examples, Preparation Examples, Formulation Examples and Test Examples, but the scope of the present invention is not to be construed as limited to these.

EXAMPLES

Example 1

Phosphoric acid mono-(2-acetyl-1H-imidazol-4-ylmethyl) ester and phosphoric acid mono-(2-acetyl-3H-imidazol-5-ylmethyl) ester (1) 4-(tert-Butyldiphenylsilyloxymethyl)-1-(2-trimethylsilylethoxy methyl)-1H-imidazole

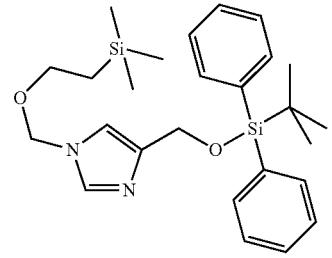

[Chemical Formula 3]

1-(2-Trimethylsilylethoxymethyl)-1H-imidazole-4-methanol (100 g, WO 01/02145) was dissolved in dichloromethane (1 L), and triethylamine (hereinafter sometimes referred to as TEA) (122 mL), 4-(N,N-dimethylamino)pyridine (hereinafter sometimes referred to as DMAP) (5.35 g) and tert-butyldiphenylsilyl chloride (hereinafter sometimes referred to as TBDPSCl) (149 mL) were added under stirring. After stirring for a day, the reaction mixture was washed with water and dried over anhydrous sodium sulfate, and the solvent was distilled off under reduced pressure. The resulting residue was purified by flash chromatography (ethyl acetate/hexane=25%→50%) using a silica gel column (trade name: Ultrapack E, manufactured by Yamazen Corporation) to give the title compound (146 g).

$^1$H-NMR (CDCl$_3$) δ: −0.01 (9H, s), 0.91 (2H, t, J=8.7 Hz), 1.08 (9H, s), 3.48 (2H, t, J=8.2 Hz), 4.75 (2H, s), 5.22 (2H, s), 6.93-6.96 (1H, m), 7.34-7.44 (6H, m), 7.50-7.52 (1H, m), 7.68-7.73 (4H, m).

(2) 1-[4-(tert-Butyldiphenylsilyloxymethyl)-1-(2-trimethylsilylethoxymethyl)-1H-imidazol-2-yl]ethanone

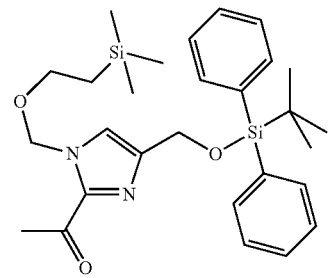

[Chemical Formula 4]

The compound obtained in (1) (30.0 g) was dissolved in tetrahydrofuran (hereinafter sometimes referred to as THF) (500 mL) and cooled to −78° C. with stirring under an argon atmosphere. n-Butyllithium (a 2.66 M hexane solution, 36.2 mL) was slowly added dropwise to this solution by using a syringe, and stirring was conducted at the same temperature for 30 minutes. N-Methoxy-N-methylacetamide (13.1 mL) was then added by using a syringe, and stirring was continued for 90 minutes. A saturated aqueous solution of ammonium chloride was added to the reaction solution to stop the reaction, and extraction was conducted by using ethyl acetate. The combined extract liquid was washed with saturated brine and dried over anhydrous sodium sulfate, and the solvent was distilled off under reduced pressure. The resulting residue was purified by flash chromatography (ethyl acetate/hexane=5%→30%) using a silica gel column (trade name: Hi-Flash column 5L, manufactured by Yamazen Corporation) to give the title compound (24.4 g).

$^1$H-NMR (CDCl$_3$) δ: −0.01 (9H, s), 0.93 (2H, t, J=7.8 Hz), 1.09 (9H, s), 2.61 (3H, s), 3.57 (2H, t, J=8.2 Hz), 4.77 (2H, s), 5.73 (2H, s), 7.20 (1H, s), 7.34-7.45 (6H, m), 7.73-7.67 (4H, m).

MS (ESI) m/z: 509 [(M+H)$^+$].

(3) 1-[4-Hydroxymethyl-1-(2-trimethylsilylethoxymethyl)-1H-imidazol-2-yl]ethanone

[Chemical Formula 5]

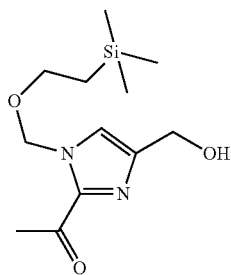

The compound obtained in (2) (24.4 g) was dissolved in THF (200 mL), tetrabutylammonium fluoride (hereinafter sometimes referred to as TBAF) (a 1.0 M THF solution, 62.7 mL) was added under stirring, and stirring was continued for 1 hour. The reaction solution was concentrated under reduced pressure, and the resulting residue was purified by flash chromatography (ethyl acetate/hexane=25%→100%) using an amino column (trade name: Hi-Flash Column 5L Amino, manufactured by Yamazen Corporation) to give the title compound (14.1 g).

$^1$H-NMR (CD$_3$OD) δ: −0.03 (9H, s), 0.90 (2H, t, J=8.0 Hz), 2.58 (3H, s), 3.59 (2H, t, J=8.0 Hz), 4.57 (2H, s), 5.73 (2H, s), 7.43 (1H, s).

MS (ESI) m/z: 271 [(M+H)$^+$].

(4) Phosphoric acid 2-acetyl-1-(2-trimethylsilylethoxymethyl)-1H-imidazol-4-ylmethyl ester di-tert-butyl ester

[Chemical Formula 6]

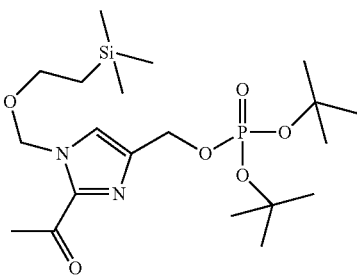

The compound obtained in (3) (2.00 g) was dissolved in a mixed solvent of dichloromethane (10 ml) and THF (10 ml), and 1H-tetrazole (1.04 g) and diisopropylphosphonous amide acid di-tert-butyl ester (3.32 ml) were added under ice cooling and stirring. After stirring for 4 hours at the same temperature, 30% aqueous hydrogen peroxide (1.46 ml) was added dropwise to the reaction solution, and stirring was continued for 17 hours while the temperature was gradually returned to room temperature. Saturated aqueous sodium thiosulfate was added to the reaction solution to thereby stop the reaction, and the reaction mixture was extracted with ethyl acetate. The extract liquid was washed with saturated brine and dried over anhydrous sodium sulfate, and the solvent was distilled off under reduced pressure. The resulting residue was purified by flash chromatography (methanol/chloroform=0%→10%) using a silica gel column (trade name: Hi-Flash Column 5L, manufactured by Yamazen Corporation) to give the title compound (3.42 g).

$^1$H-NMR (CDCl$_3$) δ: −0.01 (6H, s), 0.90-0.96 (2H, m), 1.48-1.52 (18H, m), 2.65 (3H, s), 3.54-3.59 (2H, m), 5.00 (2H, d, J=7.4 Hz), 5.74 (2H, s), 7.36 (1H, s).

MS (ESI) m/z: 463 [(M+H)$^+$].

(5) Phosphoric acid mono-(2-acetyl-1H-imidazol-4-ylmethyl) ester and phosphoric acid mono-(2-acetyl-3H-imidazol-4-ylmethyl) ester

[Chemical Formula 7]

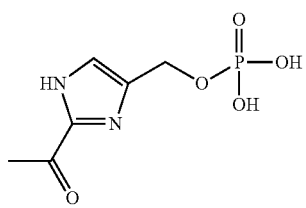

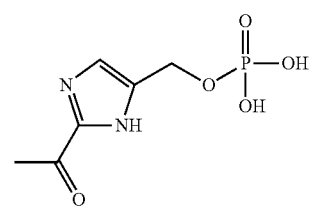

The compound obtained in (4) (3.42 g) and 4N hydrochloric acid/1,4-dioxane (10 ml) were mixed and stirred at room temperature for a day. The reaction mixture was concentrated, and the resulting residue was purified by reverse phase preparative HPLC and freeze dried to give a mixture of the title compounds (0.335 g).

$^1$H-NMR (DMSO-D$_6$) δ: 2.51 (3H, s), 4.82 (2H, d, J=7.3 Hz), 7.37 (1H, s).

MS (ESI) m/z: 221 [(M+H)$^+$].

Example 2

Phosphoric acid mono-(2-acetyl-5-methyl-1H-imidazol-4-ylmethyl) ester and phosphoric acid mono-(2-acetyl-5-methyl-3H-imidazol-4-ylmethyl) ester (1) 4-(tert-Butyldiphenylsilyloxymethyl)-5-methyl-1H-imidazole and 5-(tert-butyldiphenylsilyloxymethyl)-4-methyl-1H-imidazole

[Chemical Formula 8]

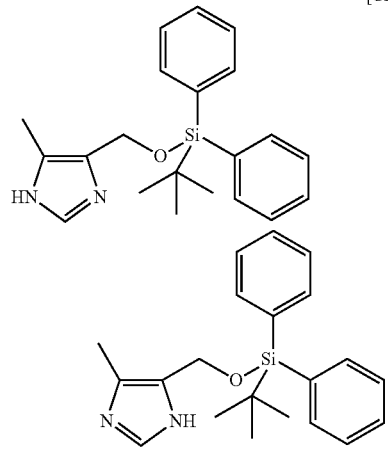

(5-Methyl-1H-imidazol-4-yl)methanol hydrochloride and (5-methyl-3H-imidazol-5-yl)methanol hydrochloride (5.00 g) were suspended in dichloromethane (100 mL), TEA (14.1 mL) and TBDPSCl (13.1 mL) were added under stirring, and stirring was continued for three days. The reaction mixture was diluted with water and extracted with chloroform. The combined extract liquid was washed with saturated brine and dried over anhydrous sodium sulfate, and the solvent was distilled off under reduced pressure. The resulting residue was purified by flash chromatography (methanol/chloroform=0%→5%) using a silica gel column (trade name: Cartridge 40M, manufactured by Biotage Ltd.) to give a mixture of the title compounds (7.77 g).

$^1$H-NMR (CDCl$_3$) δ: 1.05 (9H, s), 2.03 (3H, s), 4.68 (2H, s), 7.37-7.47 (7H, m), 7.66-7.68 (4H, m).

(2) 4-(tert-Butyldiphenylsilyloxymethyl)-5-methyl-1-(2-trimethylsilylethoxymethyl)-1H-imidazole and 5-(tert-butyldiphenylsilyloxymethyl)-4-methyl-1-(2-trimethylsilylethoxymethyl)-1H-imidazole

[Chemical Formula 9]

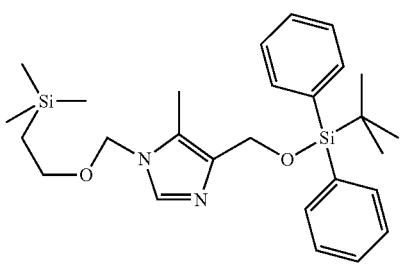

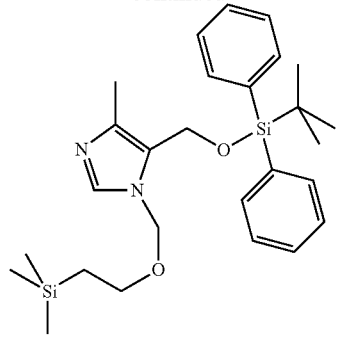

The mixture obtained in (1) (35.4 g) was dissolved in acetonitrile (500 mL), TEA (37.8 mL) and then 2-trimethylsilylethoxymethyl chloride (21.4 mL) were added under ice cooling and stirring, and stirring was conducted at 70° C. for 12 hours. The reaction mixture was allowed to cool to room temperature, and the solvent was distilled off under reduced pressure. The residue was diluted with ethyl acetate, washed with saturated brine and dried over anhydrous sodium sulfate. The solvent was distilled off under reduced pressure, and the resulting residue was purified by flash chromatography (ethyl acetate/hexane=15%→50%) using a silica gel column (trade name: Cartridge 65i, manufactured by Biotage Ltd.) to give 4-(tert-butyldiphenylsilyloxymethyl)-5-methyl-1-(2-trimethylsilylethoxymethyl)-1H-imidazole (17.9 g) as a low polarity component and 5-(tert-butyldiphenylsilyloxymethyl)-4-methyl-1-(2-trimethylsilylethoxymethyl)-1H-imidazole (9.42 g) as a high polarity component.

Low Polarity Component:

4-(tert-butyldiphenylsilyloxymethyl)-5-methyl-1-(2-trimethylsilylethoxymethyl)-1H-imidazole $^1$H-NMR (CDCl$_3$) δ: −0.02 (9H, s), 0.89 (2H, t, J=8.2 Hz), 1.04 (9H, s), 2.10 (3H, s), 3.45 (2H, t, J=8.2 Hz), 4.65 (2H, s), 5.14 (2H, s), 7.34-7.45 (3H, m), 7.70-7.75 (4H, m).
MS (ESI) m/z: 481 [M+H]$^+$.

High Polarity Component:

5-(tert-butyldiphenylsilyloxymethyl)-4-methyl-1-(2-trimethylsilylethoxymethyl)-1H-imidazole $^1$H-NMR (CDCl$_3$) δ: −0.03 (9H, s), 0.89 (2H, t, J=8.0 Hz), 1.01 (9H, s), 1.92 (3H, s), 3.46 (2H, t, J=8.3 Hz), 4.68 (2H, s), 5.38 (2H, s), 7.37-7.47 (3H, m), 7.66-7.68 (4H, m).
MS (ESI) m/z: 481 [M+H]$^+$.

(3) 1-[4-(tert-Butyldiphenylsilyloxymethyl)-5-methyl-1-(2-trimethylsilylethoxymethyl)-1H-imidazol-2-yl]ethanone

[Chemical Formula 10]

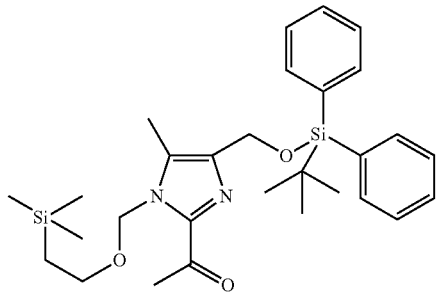

The title compound (11.7 g) was obtained in a similar manner to step (2) of Example 1 by using 4-(tert-butyldiphenylsilyloxymethyl)-5-methyl-1-(2-trimethylsilylethoxymethyl)-1H-imidazole (24.6 g) obtained in (2).

¹H-NMR (CDCl₃) δ: −0.04 (9H, s), 0.85-0.94 (2H, m), 1.05 (9H, s), 2.18 (3H, s), 2.61 (3H, s), 3.50-3.56 (2H, m), 4.72 (2H, s), 5.75 (1H, s), 7.34-7.45 (6H, m), 7.68-7.72 (4H, m).

MS (ESI) m/z: 523 [M+H]⁺.

(4) 1-[4-Hydroxymethyl-5-methyl-1-(2-trimethylsilylethoxymethyl)-1H-imidazol-2-yl]ethanone

[Chemical Formula 11]

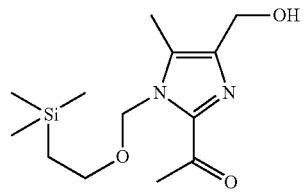

The title compound (5.41 g) was obtained in a similar manner to step (3) of Example 1 by using the compound obtained in (3) (11.7 g).

¹H-NMR (CDCl₃) δ: −0.03 (9H, s), 0.86-0.92 (2H, m), 2.24 (1H, t, J=5.5 Hz), 2.34 (3H, s), 2.64 (3H, s), 3.52-3.57 (2H, m), 4.63 (2H, d, J=6.0 Hz), 5.80 (2H, s).

MS (ESI) m/z: 285 [M+H]⁺.

(5) Phosphoric acid 2-acetyl-5-methyl-1-(2-trimethylsilylethoxymethyl)-1H-imidazol-4-ylmethyl ester di-tert-butyl ester

[Chemical Formula 12]

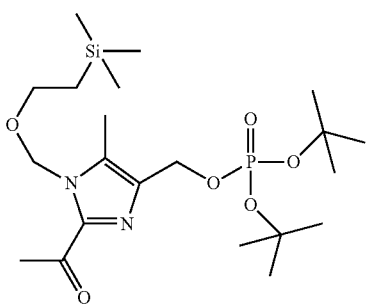

The title compound (7.32 g) was obtained in a similar manner to step (4) of Example 1 by using the compound obtained in (4) (5.00 g).

¹H-NMR (CDCl₃) δ: −0.03 (9H, s), 0.86-0.90 (2H, m), 1.43-1.53 (18H, m), 2.32-2.39 (3H, m), 2.63-2.67 (3H, m), 3.51-3.57 (2H, m), 4.95-5.08 (2H, m), 5.79-5.91 (2H, m).

MS (ESI) m/z: 477 [(M+H)⁺].

(6) Phosphoric acid mono-(2-acetyl-5-methyl-1H-imidazol-4-ylmethyl) ester and phosphoric acid mono-(2-acetyl-5-methyl-3H-imidazol-4-ylmethyl) ester

[Chemical Formula 13]

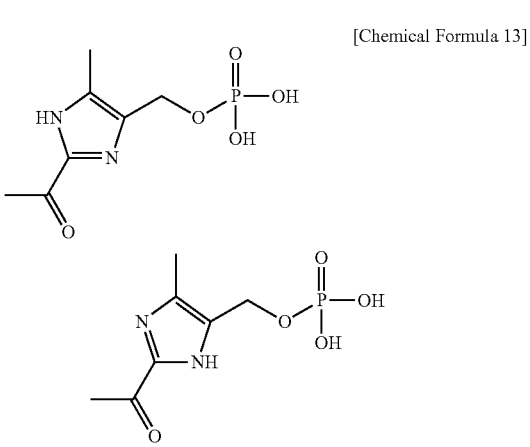

A mixture of the title compounds (0.557 g) was obtained in a similar manner to step (5) of Example 1 by using the compound obtained in (5) (3.42 g).

¹H-NMR (DMSO-D₆) δ: 2.20-2.25 (3H, m), 2.44-2.47 (3H, m), 4.77 (2H, d, J=6.4 Hz).

MS (ESI) m/z: 235 [(M+H)⁺].

Example 3

Phosphoric acid mono-(2-{1-[(Z)-hydroxyimino]-ethyl}-1H-imidazol-4-ylmethyl) ester, phosphoric acid mono-(2-{1-[(Z)-hydroxyimino]-ethyl}-3H-imidazol-4-ylmethyl) ester, phosphoric acid mono-(2-{1-[(E)-hydroxyimino]-ethyl}-1H-imidazol-4-ylmethyl) ester and phosphoric acid mono-(2-{1-[(E)-hydroxyimino]-ethyl}-3H-imidazol-4-ylmethyl) ester

[Chemical Formula 14]

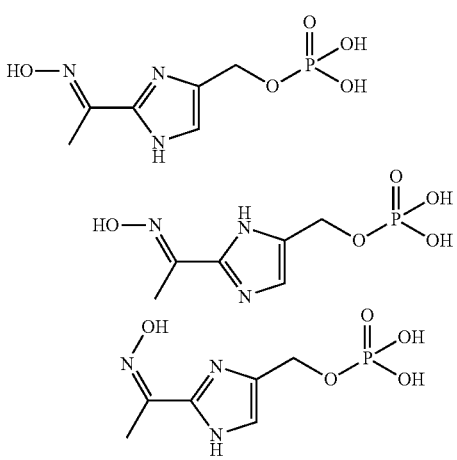

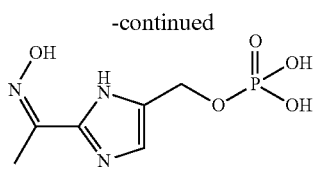

The mixture obtained in step (5) of Example 1 (25.0 mg) was dissolved in water (2.00 ml), hydroxylammonium chloride (7.89 mg) and sodium acetate (18.6 mg) were added at room temperature, and stirring was conducted for 6 hours. The insoluble substance was removed by filtration, the mother liquid was concentrated, and the resulting residue was purified by reverse phase preparative HPLC and freeze-dried to give a mixture of the title compounds (3.70 mg).

$^1$H-NMR (DMSO-D$_6$) δ: 2.17 (1H, s), 4.81 (2H, s), 7.19 (1H, s).

MS (ESI) m/z: 236 [(M+H)$^+$].

Example 4

Phosphoric acid mono-(2-isoxazol-3-yl-1H-imidazol-4-ylmethyl) ester and phosphoric acid mono-(2-isoxazol-3-yl-3H-imidazol-4-ylmethyl) ester (1) (E)-1-[4-(tert-Butyldiphenylsilyloxymethyl)-1-(2-trimethylsilylethoxymethyl)-1H-imidazol-2-yl]ethanone oxime and (Z)-1-[4-(tert-butyldiphenylsilyloxymethyl)-1-(2-trimethylsilylethoxymethyl)-1H-imidazol-2-yl]ethanone oxime

[Chemical Formula 15]

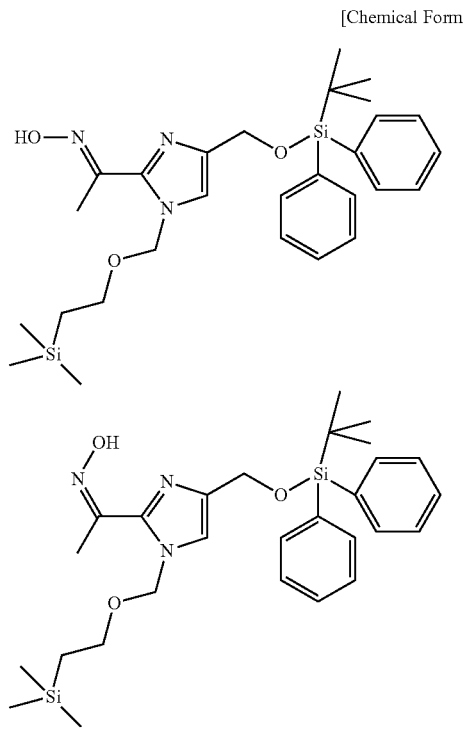

The compound obtained in step (2) of Example 1 (5.00 g) was dissolved in methanol (50 ml), hydroxylammonium chloride (680 mg) and sodium acetate (2.07 g) were added at room temperature, and stirring was conducted under warming at 50° C. for 23 hours. The reaction mixture was cooled to room temperature, the insoluble substance was removed by filtration, the mother liquid was concentrated, and the resulting residue was purified by flash chromatography (ethyl acetate/hexane=10%→70%) using a silica gel column (trade name: Hi-Flash Column 3L, manufactured by Yamazen Corporation) to give a mixture of the title compounds (4.29 g).

$^1$H-NMR (CDCl$_3$) δ: −0.01 (9H, s), 0.92 (2H, t, J=8.0 Hz), 1.08 (9H, s), 2.35 (3H, s), 3.53 (2H, t, J=7.8 Hz), 4.76 (2H, s), 5.57 (2H, s), 7.02 (1H, s), 7.33-7.45 (6H, m), 7.68-7.73 (4H, m).

MS (ESI) m/z: 524 [(M+H)$^+$].

(2) 3-[4-(tert-Butyldiphenylsilyloxymethyl)-1-(2-trimethylsilylethoxymethyl)-1H-imidazol-2-yl]isoxazole

[Chemical Formula 16]

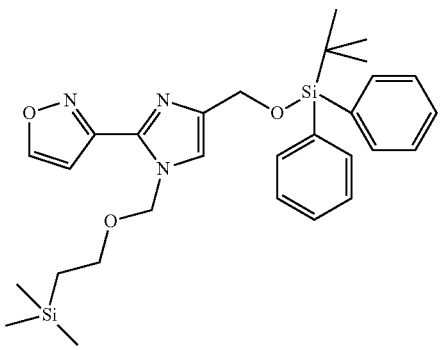

The compound obtained in step (1) (16.9 g) was dissolved in THF (300 ml) and cooled to −20° C. under stirring under nitrogen airflow. n-Butyllithium (a 2.66 M hexane solution, 60.7 ml) was added dropwise to this solution, and stirring was conducted at the same temperature for 30 minutes. N,N-Dimethylformamide (15.0 ml) was then added, and stirring was conducted at the same temperature for 1 hour. A saturated aqueous ammonium chloride solution was added to the reaction solution at the same temperature to stop the reaction. The temperature of the reaction mixture was returned to room temperature and extracted with ethyl acetate. The extract liquid was washed with saturated brine and dried over anhydrous sodium sulfate. The solvent was distilled off under reduced pressure to give a crude product of 3-[4-(tert-butyldiphenylsilyloxymethyl)-1-(2-trimethylsilylethoxymethyl)-1H-imidazol-2-yl]-4,5-dihydro-5-isoxazol-5-ol, and the crude product was then subjected to the next step.

The crude product of 3-[4-(tert-butyldiphenylsilyloxymethyl)-1-(2-trimethylsilylethoxymethyl)-1H-imidazol-2-yl]-4,5-dihydro-5-isoxazol-5-ol obtained in the previous step was dissolved in THF (300 ml) and cooled to 0° C. under nitrogen airflow under stirring. Pyridine (10.4 ml) and trifluoroacetic anhydride (17.9 ml) were added to this solution, and stirring was conducted for 30 minutes. This reaction solution was stirred for 30 minutes while the temperature of the solution was returned to room temperature, further warmed to 55° C. and stirred for 18 hours. The temperature of the reaction solution was returned to room temperature and poured into water, and the mixture was extracted with ethyl acetate. The extract liquid was washed with saturated brine and dried over anhydrous sodium sulfate, and the solvent was distilled off under reduced pressure. The resulting residue was purified by flash chromatography (ethyl acetate/hexane=10%→50%) using a silica gel column (trade name: Hi-Flash Column 3L, manufactured by Yamazen Corporation) to give the title compound (6.22 g).

$^1$H-NMR (CDCl$_3$) δ: 0.00 (9H, s), 0.97 (2H, t, J=8.5 Hz), 1.09 (9H, s), 1.26 (2H, t, J=6.9 Hz), 3.63 (2H, t, J=8.9 Hz), 4.89 (2H, s), 5.87 (2H, s), 7.35-7.48 (6H, m), 7.63-7.68 (4H, m), 8.61 (1H, s).

MS (ESI) m/z: 534 [(M+H)$^+$].

(3) [2-(Isoxazol-3-yl)-1-(2-trimethylsilylethoxymethyl)-1H-imidazol-4-yl]methanol

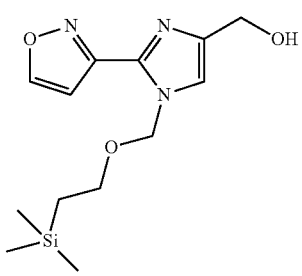

[Chemical Formula 17]

The compound obtained in step (2) (6.22 g) was dissolved in THF (200 ml), TBAF (a 1.0 M THF solution, 11.6 ml) was added under stirring, and stirring was conducted for 4 hours. The reaction solution was concentrated under reduced pressure, and the resulting residue was purified by flash chromatography (ethyl acetate/hexane=50%→100%) using an amino column (trade name: Hi-Flash Column 3L Amino, manufactured by Yamazen Corporation) to give the title compound (1.61 g).

$^1$H-NMR (CDCl$_3$) δ: −0.05 (9H, s), 0.92 (2H, t, J=8.3 Hz), 2.10 (1H, s), 3.58 (2H, t, J=8.3 Hz), 4.68 (2H, d, J=5.5 Hz), 5.80 (2H, s), 6.97 (1H, d, J=1.8 Hz), 7.19 (1H, s), 8.45 (1H, d, J=1.8 Hz).

MS (ESI) m/z: 296 [(M+H)$^+$].

(4) Phosphoric acid di-tert-butyl ester [2-(isoxazol-3-yl)-1-(2-trimethylsilanylethoxymethyl)-1H-imidazol-4-yl]methyl ester

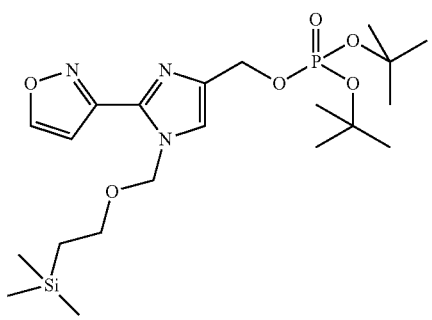

[Chemical Formula 18]

The compound obtained in step (3) (1.61 g) and 1H-tetrazole (760 mg) were dissolved in THF (20 ml), di-tert-butyl N,N-diisopropylphosphoramidite (2.45 ml) was added at room temperature under stirring, and stirring was conducted for 2 hours. This reaction solution was cooled to 0° C., 30% aqueous hydrogen peroxide (0.250 ml) was added, and stirring was conducted for 14 hours while the temperature was gradually returned to room temperature. A saturated aqueous sodium thiosulfate solution was added to the reaction solution to stop the reaction, and the reaction mixture was extracted with ethyl acetate. The extract liquid was washed with saturated brine and dried over anhydrous sodium sulfate, and the solvent was distilled off under reduced pressure. The resulting residue was purified by flash chromatography (ethyl acetate/hexane=10%→50%) using a silica gel column (trade name: SNAP Cartridge KP-Sil 100 g, manufactured by Biotage Ltd.) to give the title compound (2.21 g).

$^1$H-NMR (CDCl$_3$) δ: −0.05 (9H, s), 0.91 (2H, t, J=7.6 Hz), 1.45-1.58 (18H, m), 3.53-3.60 (2H, m), 5.02 (2H, d, J=7.8 Hz), 5.79 (2H, s), 6.94-6.95 (1H, m), 7.29 (1H, s), 8.44 (1H, t, J=1.8 Hz).

MS (ESI) m/z: 488 [(M+H)$^+$].

(5) Phosphoric acid mono-(2-isoxazol-3-yl-1H-imidazol-4-ylmethyl) ester and phosphoric acid mono-(2-isoxazol-3-yl-3H-imidazol-4-ylmethyl) ester

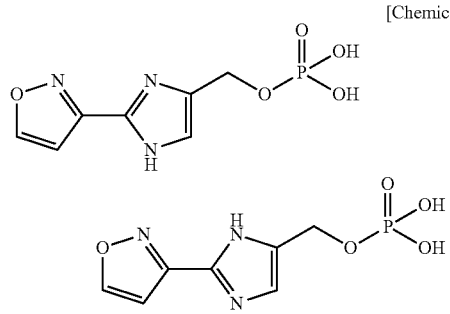

[Chemical Formula 19]

The compound obtained in step (4) (1.97 g) was dissolved in a 4 N hydrochloric acid/1,4-dioxane solution (45 ml), warmed to 45° C. and stirred for 6 hours. The reaction solution was allowed to cool, and the solvent was distilled off under reduced pressure. The resulting residue was purified by reverse phase preparative HPLC and freeze-dried to give a mixture of the title compounds (348 mg).

$^1$H-NMR (DMSO-D$_6$) δ: 3.34 (2H, br s), 4.82 (2H, d, J=6.9 Hz), 6.93 and 6.97 (total 1H, each d, J=1.4 and 2.3 Hz, respectively), 7.29 (1H, br s), 9.00 and 9.04 (total 1H, each d, J=2.3 and 2.8 Hz respectively).

MS (ESI) m/z: 246 [(M+H)$^+$].

Formulation Example 5 g of the compound obtained in the Examples, 90 g of lactose, 34 g of corn starch, 20 g of crystalline cellulose and 1 g of magnesium stearate are mixed in a blender and compressed by a tabletting machine to give tablets.

Test Example 1

Variation in Number of Lymphocytes in Peripheral Blood in Rat

Male LEW/Crj rats at 3 or 6 weeks old were purchased from Charles River Laboratory Japan Inc. The rats were acclimatized for a week before the start of experiments. The rats were used for the experiments at 3 or 5 rats per one group. A necessary amount of a compound was weighed and suspended in a 0.5% MC solution by using a mortar and a muddler, or a homogenizer. A liquid for administration was prepared so as to be 5 mL per 1 kg body weight. The prepared solution was administered once by oral gavage. The rats were abdominally dissected before the oral administration and 1, 3, 7, 8, 24 or 48 hours after the oral administration under diethyl ether anesthesia or under isoflurane anesthesia, and 2 mL of the blood was drawn from the inferior vena cava. The blood was immediately put into a vacuum-sealed blood collection tube coated with an anticoagulant (EDTA-2K) (Nipro Corporation) and mixed. The sample was handled under room temperature condition until measurement. The number of the lymphocytes was measured by using an automatic hemacytometer (ADVIA120, Siemens Healthcare Diagnostics K. K.). At the time of blood collection, the thymus gland was also excised.

The compounds of Examples 1, 2 and 4 reduced the number of lymphocytes in the peripheral blood.

Test Example 2

S1P Lyase Inhibitory Ability in Rat

The excised thymus gland was crushed by either a method including using zirconia beads in the presence of a homogenize buffer (50 mM HEPES-NaOH (pH=7.4), 0.15 M NaCl, 10% Glycerol, 1 mM EDTA, 1 mM DTT and complete protease inhibitor cocktail (Roche, #4693132)) or a method including chopping up the thymus gland and thereafter using a Potter-Elvehjem homogenizer. Furthermore, the crushed product was sonicated by a sonicator and centrifuged at 4° C. and 1,000 G for 3 minutes, and the supernatant was collected. The protein amount in the supernatant was quantified by the Bradford method, and the supernatant was flash-freezed with liquid nitrogen and then stored at −80° C. (thymus gland extract).

In order to measure S1P lyase activity, the thymus gland extract was diluted with a homogenize buffer, and reacted at 37° C. for 1 hour in an enzyme reaction solution containing [$^3$H]dh S1P (3.4 nM) as substrate (0.1M K-Pi (pH=7.4), 25 mM NaF, 5 mM Na$_3$VO$_4$, 1 mM EDTA, 1 mM DTT, 0.1% Triton X-100, 2 μM cold dhS1P). The thymus gland extract reacted on ice for 1 hour was used as a negative control. After the reaction, sodium hydroxide was added so that the final concentration became 0.1 M, and an equivalent amount of a mixed solution CHCl$_3$/MeOH (2:1) was further added, stirring was conducted, centrifugation was conducted at room temperature and 8,400 G for 3 minutes, the aqueous layer part was then collected, and radioactivity was measured by a liquid scintillation counter.

The compounds of Examples 1 and 2 decreased SIP lyase activity in the thymus gland.

Test Example 3

S1P Lyase Inhibitory Ability in Mouse

Male BALB/c mice at 6 weeks old are purchased from Charles River Laboratory Japan Inc. The mice are acclimatized for a week, and the mice at 7 weeks old are used in experiments. The mice are used for the experiments at 5 mice per one group. A necessary amount of a compound is weighed and suspended in a 0.5% MC solution by using a mortar and a muddler. A liquid for administration is prepared so as to be 10 mL per 1 kg body weight. The prepared solution is administered once by oral gavage.

Ethylenediamine tetraacetic acid dihydrogen dipotassium (EDTA-2K, NACALAI TESQUE, INC.) is dissolved in water for injection so as to be 5% (5% EDTA-2K solution). The mice are abdominally dissected before the oral administration and 1, 3, 7, 8, 24 or 48 hours after the administration under diethyl ether anesthesia, and 0.5 mL of the blood is drawn from the inferior vena cava by using a syringe through which a 5% EDTA-2K solution has been passed in advance. At this time, the thymus gland is also excised. The blood sample is handled under room temperature condition until measurement. The number of the lymphocytes is measured by using an automatic hemacytometer (ADVIA120, Siemens Healthcare Diagnostics K. K.).

The excised thymus gland is crushed by either a method including using zirconia beads in the presence of a homogenize buffer (50 mM HEPES-NaOH (pH=7.4), 0.15 M NaCl, 10% Glycerol, 1 mM EDTA, 1 mM DTT and complete protease inhibitor cocktail (Roche, #4693132)) or a method including chopping up the thymus gland and thereafter using a Potter-Elvehjem homogenizer. Furthermore, the crushed product is sonicated by a sonicator and centrifuged at 4° C. and 1,000 G for 3 minutes, and the supernatant is collected. The protein amount in the supernatant is quantified by the Bradford method, and the supernatant is flash-freezed with liquid nitrogen and then stored at −80° C. (thymus gland extract).

In order to measure S1P lyase activity, the thymus gland extract is diluted with a homogenize buffer, and reacted at 37° C. for 1 hour in an enzyme reaction solution containing [$^3$H]dh S1P (3.4 nM) as a substrate (0.1M K-Pi (pH=7.4), 25 mM NaF, 5 mM Na$_3$VO$_4$, 1 mM EDTA, 1 mM DTT, 0.1% Triton X-100, 2 μM cold dhS1P). The thymus gland extract reacted on ice for 1 hour is used as a negative control. After the reaction, sodium hydroxide is added so that the final concentration becomes 0.1 M, and an equivalent amount of a mixed solution CHCl$_3$/MeOH (2:1) is further added and stirring is conducted, centrifugation is conducted at room temperature and 8,400 G for 3 minutes, the aqueous layer part is collected, and radioactivity is measured by a liquid scintillation counter.

Test Example 4

Tests in Pathologic Models

Using pathological models such as experimental autoimmune encephalomyelitis (Clin. Exp. Immunol., 120, 526-531 (2000), J. Neuroimmunol., 129, 1-9 (2002), Annu. Rev. Immunol., 10, 153-187 (1992), Eur. J. Immunol., 25, 1951-1959 (1995)), collagen-induced arthritis (Current Protocols in Immunology (1996) 15.5.1-15.5.24), aspirin-induced asthma (Arthritis Rheum. 2010 January; 62 (1): 82-92), GPI-induced arthritis (Arthritis Res Ther. 2008; 10 (3): R66. Epub 2008 Jun. 5.), antibody-induced arthritis (J. Immunol. 2003 Apr. 15; 170 (8): 4318-24.), psoriasis (J. Immunol. 2009 May 1; 182 (9): 5836-45., J Clin Invest. 2008 February; 118 (2): 597-607., Nature 2007 445: 648-651.), inflammatory bowel diseases (Current Protocols in Immunology (2001) 15.19.1-15.19.14, Proc Natl Acad Sci USA. 2009 Mar. 3; 106 (9): 3300-5. Epub 2009 Feb. 6.), systemic lupus erythematosus (Current Protocols in Immunology (2002) 15.20.1-15.20.22), acute pulmonary disorders (Am. J. Respir. Cell Mol. Biol. 2010 Dec. 10 as doi: 10.1165/rcmb. 2010-0422OC) and cardiac ischemia-reperfusion disorders (Am J Physiol Heart Circ Physiol (2011) May; 300 (5): H1753-61), the pharmacological effects of the compounds are evaluated.

INDUSTRIAL APPLICABILITY

According to the present invention, a pharmaceutical composition for preventing or treating inflammatory bowel diseases, acute pulmonary disorders, ischemia-reperfusion disorders, autoimmune diseases, multiple sclerosis or allergic diseases or for suppressing implant rejection responses can be provided.

The invention claimed is:

1. A compound of general formula (I):

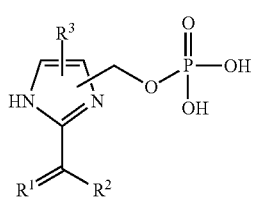

or a pharmaceutically acceptable salt thereof, wherein
$R^1$ is an oxygen atom or N—OH,
$R^2$ is a methyl group, or
$R^1$ and $R^2$ together with the carbon atom to which they are bonded form

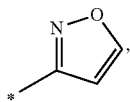

and
$R^3$ is a hydrogen atom or a methyl group.

2. A compound selected from:
phosphoric acid mono-(2-acetyl-1H-imidazol-4-ylmethyl) ester,
phosphoric acid mono-(2-acetyl-3H-imidazol-4-ylmethyl) ester,
phosphoric acid mono-(2-acetyl-5-methyl-1H-imidazol-4-ylmethyl) ester,
phosphoric acid mono-(2-acetyl-5-methyl-3H-imidazol-4-ylmethyl) ester,
phosphoric acid mono-(2-{1-[(Z)-hydroxyimino]-ethyl}-1H-imidazol-4-ylmethyl) ester,
phosphoric acid mono-(2-{1-[(Z)-hydroxyimino]-ethyl}-3H-imidazol-4-ylmethyl) ester,
phosphoric acid mono-(2-{1-[(E)-hydroxyimino]-ethyl}-1H-imidazol-4-ylmethyl) ester,
phosphoric acid mono-(2-{1-[(E)-hydroxyimino]-ethyl}-3H-imidazol-4-ylmethyl) ester,
phosphoric acid mono-(2-isoxazol-3-yl-1H-imidazol-4-ylmethyl) ester,
phosphoric acid mono-(2-isoxazol-3-yl-3H-imidazol-4-ylmethyl) ester, and
pharmaceutically acceptable salts of any of the foregoing.

3. A pharmaceutical composition comprising the compound or pharmaceutically acceptable salt thereof of claim 1 and a pharmacologically acceptable carrier.

4. A method of treating a disease or for suppressing implant rejection response, comprising administering the pharmaceutical composition of claim 3 to a subject in need thereof, wherein the disease is selected from: an inflammatory bowel disease, an ischemia-reperfusion disorder, rheumatoid arthritis, multiple sclerosis, and an allergic disease selected from the group consisting of atopic dermatitis, allergic rhinitis, allergic gastroenteritis, bronchial asthma, infantile asthma, food allergy, drug allergy, and urticaria.

5. The method of claim 4, wherein the inflammatory bowel disease is ulcerative colitis or Crohn's disease.

6. The method of claim 4, wherein the disease is rheumatoid arthritis.

7. The method of claim 4, wherein the disease is an allergic disease selected from atopic dermatitis, allergic rhinitis, allergic gastroenteritis, bronchial asthma, infantile asthma, food allergy, drug allergy and urticaria.

8. A method of treating an inflammatory bowel disease, an ischemia-reperfusion disorder, rheumatoid arthritis, multiple sclerosis, or an allergic disease selected from the group consisting of atopic dermatitis, allergic rhinitis, allergic gastroenteritis, bronchial asthma, infantile asthma, food allergy, drug allergy, or urticaria, or for suppressing implant rejection response, comprising administering a therapeutically effective amount of the compound, or pharmaceutically acceptable salt thereof, of claim 1 to a mammal.

9. The method of claim 8, wherein the mammal is a human.

10. A method of treating an inflammatory bowel disease, an ischemia-reperfusion disorder, rheumatoid arthritis, multiple sclerosis, or an allergic disease selected from the group consisting of atopic dermatitis, allergic rhinitis, allergic gastroenteritis, bronchial asthma, infantile asthma, food allergy, drug allergy, or urticaria, or for suppressing implant rejection response, comprising administering a therapeutically effective amount of the compound or pharmaceutically acceptable salt thereof of claim 2 to a mammal.

11. The method of claim 10, wherein the mammal is a human.

12. A pharmaceutical composition comprising the compound or pharmaceutically acceptable salt thereof according to claim 2 and a pharmacologically acceptable carrier.

13. A method of treating a disease or for suppressing implant rejection response, comprising administering the pharmaceutical composition of claim 12 to a subject in need thereof; wherein the disease is selected from the group consisting of an inflammatory bowel disease, an ischemia-reperfusion disorder, rheumatoid arthritis, multiple sclerosis, and an allergic disease selected from the group consisting of atopic dermatitis, allergic rhinitis, allergic gastroenteritis, bronchial asthma, infantile asthma, food allergy, drug allergy, or urticaria.

14. The method of claim 13, wherein the inflammatory bowel disease is ulcerative colitis or Crohn's disease.

15. The method of claim 13, wherein the disease is rheumatoid arthritis.

16. The method of claim 13, wherein the disease is an allergic disease selected from atopic dermatitis, allergic rhinitis, allergic gastroenteritis, bronchial asthma, infantile asthma, food allergy, drug allergy or urticaria.

* * * * *

UNITED STATES PATENT AND TRADEMARK OFFICE
CERTIFICATE OF CORRECTION

| | |
|---|---|
| PATENT NO. | : 9,120,835 B2 |
| APPLICATION NO. | : 14/129596 |
| DATED | : September 1, 2015 |
| INVENTOR(S) | : Nobuo Machinaga et al. |

It is certified that error appears in the above-identified patent and that said Letters Patent is hereby corrected as shown below:

On the title page, at (73) Assignee, delete "Daiichi Sankyo Company Limited" and insert therefor -- Daiichi Sankyo Company, Limited --.

Claims

In claim 8, in column 20, at line 21, delete "drug allergy, or urticaria" and insert therefor -- drug allergy, and urticaria --.

In claim 10, in column 20, at line 31, delete "drug allergy, or urticaria" and insert therefor -- drug allergy, and urticaria --.

In claim 13, in column 20, at line 50, delete "or urticaria" and insert therefor -- and urticaria --.

In claim 16, in column 20, at line 58, delete "drug allergy or urticaria" and insert therefor -- drug allergy and urticaria --.

Signed and Sealed this
Sixteenth Day of February, 2016

Michelle K. Lee
*Director of the United States Patent and Trademark Office*